United States Patent
Kautzer et al.

(10) Patent No.: US 7,091,491 B2
(45) Date of Patent: Aug. 15, 2006

(54) METHOD AND MEANS FOR REDUCING ELECTROMAGNETIC NOISE INDUCED IN X-RAY DETECTORS

(75) Inventors: Jeffrey A. Kautzer, Pewaukee, WI (US); Richard Gordon Cronce, New Berlin, WI (US); Olgun Kukrer, Waukesha, WI (US)

(73) Assignee: General Electric Company, Schenectady, NY (US)

(*) Notice: Subject to any disclaimer, the term of this patent is extended or adjusted under 35 U.S.C. 154(b) by 119 days.

(21) Appl. No.: 10/846,971

(22) Filed: May 14, 2004

(65) Prior Publication Data

US 2005/0254624 A1 Nov. 17, 2005

(51) Int. Cl.
*G01T 1/24* (2006.01)
*H01L 27/00* (2006.01)
*H01L 27/146* (2006.01)
*G21K 7/00* (2006.01)

(52) U.S. Cl. .............. 250/370.09; 378/98.7; 378/91; 378/21

(58) Field of Classification Search ........... 378/98.7; 250/370, 370.09
See application file for complete search history.

(56) References Cited

U.S. PATENT DOCUMENTS

| | | | | |
|---|---|---|---|---|
| 5,590,168 A | * | 12/1996 | Iketaki | 378/43 |
| 5,648,660 A | * | 7/1997 | Lee et al. | 250/370.09 |
| 5,650,616 A | * | 7/1997 | Iketaki | 250/288 |
| 6,377,041 B1 | * | 4/2002 | Jones et al. | 324/244 |
| 6,453,008 B1 | * | 9/2002 | Sakaguchi et al. | 378/98.7 |
| 2005/0207539 A1 | * | 9/2005 | Poppleton | 378/157 |

* cited by examiner

*Primary Examiner*—Alan Cariaso
*Assistant Examiner*—Mary Zettl
(74) *Attorney, Agent, or Firm*—McAndrews, Held & Malloy, Ltd.; Peter J. Vogel; Michael A. Dellapenna

(57) ABSTRACT

The present invention relates to a system and method by which the magnitude of an interfering electrical and/or magnetic field may be sampled locally (in the X-ray detector for example) and reduced or eliminated. More specifically, embodiments comprise a system and method by which an interfering field may be sampled within the same orientation as the X-ray detector panel, and then subtracted out of each respective element sample.

19 Claims, 10 Drawing Sheets

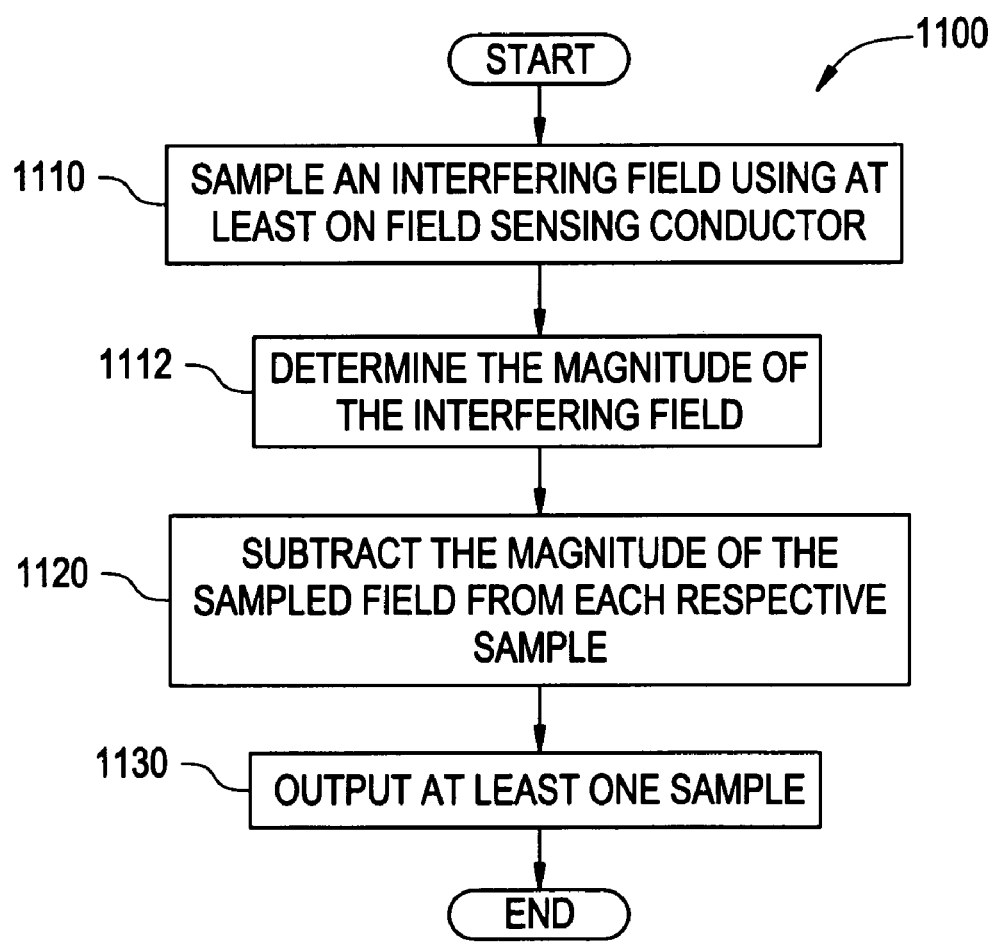

METHOD AND MEANS FOR REDUCING ELECTROMAGNETIC NOISE INDUCED IN X-RAY DETECTORS

BACKGROUND OF THE INVENTION

This application is directed in general to the design and manufacture of an X-ray detector and an X-ray detector formed thereby. Specifically, this application is directed to the design and manufacture of flat panel X-ray detectors and the flat panel X-ray detectors formed thereby, which in turn may be used in medical imaging systems, devices or other apparatus for example.

It should be appreciated that engineering and manufacturing flat panels adapted to be used in X-ray detectors for example, is a complex endeavor. Solid state X-ray imaging technology has steadily advanced due in part to the development of photo sensitive semiconductor arrays using either indirect X-ray-to-light scintillation panels (Amorphous Silicon with CsI for example) or direct X-ray conversion panels (Amorphous SE, PbO or Hgl for example). It is contemplated that one or more of those technologies may use transistor switches (TFT-FETs for example) providing effective multiplexing of a pixel array, enabling board analog-digital conversion to be performed using a smaller number of converters in comparison to the total number of converters than the total number of pixels in a given X-ray detector panel.

It is further contemplated that one or more of these technologies may use deposited metal lines (conduction paths formed by sputtering Mo, Al, Cu or other conductor metals for example) forming data and scan lines in a grid of rows and columns, facilitating the control of the TFTs (in one direction) while carrying a charge from the photo elements (in a different or opposing direction). As the X-ray detector panel pixel sizes decrease, and panel sizes increase, the ratio of signal (charge) to path length from photo sensor to the A/D converter dramatically decreases. This phenomenon is found to be true for both X-ray and CT detectors.

At the same time, in order to handle the smaller and lengthier data line paths and still produce acceptable image quality, the design of the A/D conversion system has become increasingly complex. It is contemplated that, in order to produce acceptable Signal to Noise Ration ("SNR"), noise levels well below about 2000 electrons are not uncommon in these types of systems. However, such complex solid state systems have become inherently more susceptible to electric and/or magnetic (referred to as Electro-Magnetic or "EM") noise induced onto the photo sensor panel (induced primarily onto the data line paths).

Effectively shielding high frequency, Electro-Magnetic noise has been shown to be feasible, but not without some level of X-ray photon attenuation into the X-ray sensitive surface of the detector. Effective shielding of low and high frequency, Electro-Magnetic noise is not possible using current materials, as low frequency magnetic fields require metallic elements which greatly attenuate X-ray photons in medical applications. For example, EM noise has been shown to be at sufficient levels to effect images within certain solid state X-ray systems which are in close proximity to organ and catheter navigational systems, pace maker placement and programming systems, magnetic catheter drive systems as well as RF ablation systems. These types of systems may cause electric and/or magnetic or EM field strengths well in excess of those required for susceptibility testing as part of the international certification.

BRIEF SUMMARY OF THE INVENTION

One embodiment comprises a system and method by which the amplitude/magnitude of an interfering electrical and/or magnetic or EM field may be sampled locally (in the X-ray detector for example) and reduced or eliminated. More specifically, embodiments comprise a system and method by which an interfering field may be sampled within the same orientation as the X-ray detector panel, and then subtracted out of each respective element sample.

One embodiment comprises an X-ray detector having one or more field sensing conductors in the same orientation as the panel data lines. It is contemplated that in at least one embodiment, field sensing conductors may be oriented in the TFT scan line direction as well. The interfering field is sampled locally by one or more of these conductors, which have essentially the same resistance and capacitance as the ordinary data lines. The field amplitude of the interfering field may be subtracted out in a pre-amplification stage. Embodiments are also contemplated in which the amplitude of the interfering field may be digitized and then subtracted out using digital processing.

One embodiment relates to method for reducing electromagnetic noise induced in an X-ray detector. This embodiment comprises locally sampling an interfering field in the X-ray detector and subtracting an amplitude/magnitude of the sampled interfering field from at least one element sample. The method further comprises outputting at least one sample having reduced EM noise.

Other embodiments relate to a method comprising sampling an interfering field using at least one field sensing conductor formed in the X-ray detector. The interfering field may be sampled within a same orientation as the X-ray detector. Embodiments further comprise subtracting the amplitude/magnitude of the sampled interfering field from each respective element sample (using, for example, an analog-digital conversion system, a pre-amplification stage and/or by digitizing the magnitude of the interfering field and then subtracting the magnitude using digital processing). In at least one embodiment, the X-ray detector is used in a medical imaging system.

Another embodiment relates to a method of reducing induced EM noise in an X-ray detector used in a medical imaging system. This method comprises locally sampling an interfering field using at least one field sensing conductor and determining an amplitude/magnitude of the sampled interfering field. The amplitude/magnitude of the sampled interfering field is subtracted from each respective element sample (using, for example, an analog-digital conversion system, a pre-amplification stage and/or by digitizing the magnitude of the interfering field and then subtracting the amplitude/magnitude using digital processing) and the respective element sample having reduced EM noise is output.

Yet another embodiment relates to a method of forming an X-ray detector. This embodiment comprises determining at least one of a number of field sensing conductors and a spacing of the field sensing conductors based at least in part on an interfering field. The X-ray detector is formed having at least one of the determined number of field sensing conductors and the determined spacing.

Other embodiments comprise determining a highest frequency of the interfering field. The sensing conductors are spaced a minimum of about one fourth of a wavelength of the highest frequency of the interfering field. Further, the field sensing conductors are added in a same orientation as at least one of data and scan lines formed in the X-ray detectors.

Yet another embodiment relates to a method of forming an X-ray detector. This embodiment comprises determining an interfering field and the highest frequency of the interfering field. A wavelength of the highest frequency of the interfering field is determined. A number of field sensing conductors and/or a spacing of the field sensing conductors may be determined, based at least in part, on the wavelength of the highest frequency of the interfering field. The X-ray detector is formed having the number of field sensing conductors and the determined spacing. In at least one embodiment, the field sensing conductors are added in a same orientation as at least one of data and scan lines formed in the X-ray detector.

Still another embodiment relates to an X-ray detector used in a medical imaging system. In this embodiment, the X-ray detector comprises a panel portion, at least one edge finger contact and a readout electronics portion. The at least one field sensing conductor is adapted to reduce electromagnetic noise induced in the X-ray detector. The at least one edge finger contact is coupled to at least a portion of the panel portion and the readout electronics portion.

Embodiments relate to an X-ray detector comprising a plurality of field sensing conductors, wherein at least of the field sensing conductors is spaced a minimum of about one fourth of a wavelength of a highest frequency of the sample interfering field from another of the interfering field sensing conductors. At least one of the field sensing conductor is in a same orientation as at least one of a data line and scan line formed in the X-ray detector.

In at least one embodiment of the X-ray detector, the interfering field may be sampled within a same orientation as the X-ray detector. The readout electronics portion comprises an analog-digital conversion system adapted to subtract out a magnitude of the interfering field. The magnitude of the interfering field may be subtracted out in a pre-amplification stage in the analog-digital conversion system. Further, the analog-digital conversion system may comprises a digital processing system adapted to digitize the magnitude of the interfering field and then subtracting out the magnitude using digital processing.

BRIEF DESCRIPTION OF SEVERAL VIEWS OF THE DRAWINGS

FIG. 11 illustrates a detailed flow diagram depicting a method of using an X-ray detector (similar to that illustrated in FIG. 6) adapted to be used with a medical imagining system (similar to that illustrated in FIG. 1) in accordance with certain embodiments.

Figure 1:
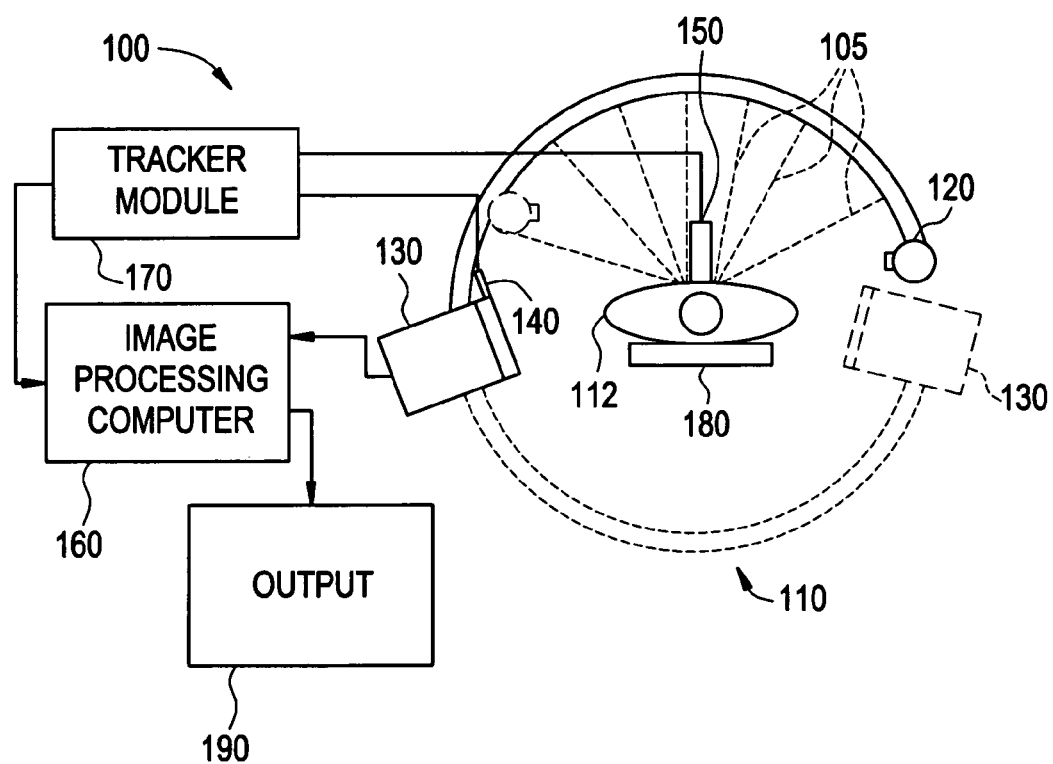
FIG. 1 illustrates a medical imaging system, device, machine or apparatus used in accordance with certain embodiments.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

For the purpose of illustration only, the following detailed description references certain embodiments of an X-ray detector (a flat panel X-ray detector) used in a medical imaging system, device, machine or apparatus. However, it is understood that the present invention may be used with other devices or systems.

It should be appreciated that the engineering and manufacture of active or flat panels, used in X-ray detectors for example, is a complex endeavor. Such engineering and manufacturing process requires knowledge of amorphous or single/poly crystaline semiconductor devices such as Thin Film Transistors Field Effect Transistors (TFT FET) and wide bandgap Photodiodes for example. Deposition processes such as Plasma Enhanced Chemical Vapor Deposition (alternatively referred to as "PECVD") and sputtering for example are used to produce interconnecting metal, device structures, X-ray converters and other structures in such engineering and manufacturing processes.

It is known that electric and/or magnetic field lines of a given frequency generated by, for example, organ and catheter navigational systems, pace maker placement and programming systems, magnetic catheter drive systems, and RF ablation systems or other components of imaging systems may pass through an X-ray detector causing signal noise on at least the detector data lines. EM field lines of force may pass through the X-ray detector, causing signal noise on the data lines. Such magnetic field lines of force may pass through the circuit loop of the TFT-diode, data line, analog-digital converter and ground return. This in turn may induce current to flow through the circuit loop, which is digitized as uncorrelated structured noise, producing an image artifact in the generated image. The resulting image artifact is dependent upon for example, the induced filed strength and frequency, overall detector size and orientation within the field.

One embodiment comprises a system and method by which the magnitude of the interfering EM field may be sampled locally (in the X-ray detector for example) and reduced or eliminated. More specifically, embodiments comprise a system and method by which an interfering field may be sampled within the same orientation as the X-ray detector panel, and then subtracted out of each respective element sample. One embodiment comprises an X-ray detector having one or more field sensing conductors in the same orientation as the panel data lines. It is contemplated that in at least one embodiment, field sensing conductors may be oriented in the TFT scan line direction as well. The interfering field is sampled locally by one or more of these conductors, which have essentially the same resistance and capacitance as the data lines. The field amplitude/magnitude of the interfering field is subtracted out in a pre-amplification stage in the conversion electronics. It is also contemplated that the amplitude/magnitude of the interfering field may be digitized and then subtracted out using digital processing.

FIG. 1 illustrates a medical imaging system, device, machine or apparatus, generally designated 100, used in accordance with one embodiment. It is contemplated that system 100 may comprise a variety of imaging systems including an X-ray system, a CT system, an EBT system, an ultrasound system, an MR system, or other imaging system.

In at least one embodiment, system 100 includes a C-arm 110, one or more X-ray sources 120, one or more X-ray detectors 130 (flat panel X-ray detectors for example), one or more electromagnetic (EM) sensors 140, an EM transmitter 150, an image processing computer 160, a tracker module 170, a positioning device 180, and an output 190. In the illustrated embodiment, tracker module 170 is depicted communicating with at least EM sensor 140, EM transmitter 150, and image processing computer 160. FIG. 1 further illustrates image processing computer 160 communicating with at least X-ray detector 130, tracker module 170 and output 190.

In at least one embodiment, X-ray source 120 and X-ray detector 130 are mounted on opposing sides of the C-arm 110. The X-ray source 120 and X-ray detector 130 may be movably mounted on the C-arm 110. In one embodiment, EM sensor 140 is mounted on X-ray detector 130. The EM transmitter 150 is positioned on an object 112, such as a patient, to be imaged. Alternatively, EM transmitter 150 may be located on the X-ray detector 130, and EM sensor 140 may be located on an object or patient 112 being imaged. The object or patient 112 is positioned on or in positioning device 180. In at least one embodiment, positioning device 180 comprises a table, a table bucky, a vertical bucky, a support or other positioning device adapted to be used.

In at least one embodiment, C-arm 110 is movable in several directions along multiple image acquisition paths, including, for example, an orbital direction, a longitudinal direction, a lateral direction, a transverse direction, a pivotal direction and a "wig-wag" direction. In at least one embodiment, X-ray source 120 and detector 130 are movably positioned on C-arm 110. Thus, the C-arm 110, along with X-ray source 120 and X-ray detector 130, may be moved and positioned about the positioning device 180 on or in which object 112 has been situated.

The C-arm 110 is used to position the X-ray source 120 and detector 130 about object 112 so that one or more X-rays 105 (or other energy) may irradiate object 112 for use in producing one or more images. The C-arm 110 may be moved or re-positioned at a variety of scan angles around object 112, obtaining a plurality of images. As the C-arm 110 moves, the distance between the X-ray detector 130 and the object 112 may vary. Further, the distance between X-ray source 120 and object 112 may also vary.

It is contemplated that, in at least one embodiment, X-ray source 120 and detector 130 on C-arm 110 may move in a cross-arm or orbital motion, for example. In an orbital motion, the X-ray source 120 and the detector 130 do not move in a circular path. In tomographic image reconstruction using orbital motion, a distance between detector 130 and object 112 (and a distance between source 120 and object 112) may vary during collection of projection images.

In at least one embodiment, a position of the X-ray detector 130 may be recorded for one or more projection images. Additionally, a distance between detector 130 and the X-ray source 120 may be determined. A magnification change may be quantified and compensated for during tomographic image reconstruction using detector 130 position and detector-to-object distance. The EM sensor 140 or other tracking device may be placed on detector 130. The EM transmitter 150 or other tracking device may be placed on the object 112. Data from the sensor 140 and transmitter 150 may be used to determine a position of detector 130 during a trajectory of detector 130. Other tracking devices, such as optical or mechanical tracking devices, may be used to determine a position of one or more components in the system 100.

In at least one embodiment, transmitter 150 broadcasts a signal, such as a magnetic field, that is detected by sensor 140. The tracker module 170 may use data from the transmitter 150 to determine a position of the detector 130 with respect to object 112. Differences in position and, thus, distance between the detector 130 and the object, correspond to differences in magnification in obtained X-ray projection images.

Changing the distance between detector 130 and object 112 and/or the distance between the source 120 and object 112 changes the magnification of the object projected onto the detector for point sources or near-point sources that emit non-parallel beams, such as X-rays. If the field of view of the X-ray source 120 is constant, as an object approaches the X-ray source 120, the object occupies more of the field of view and therefore projects as a larger image onto the detector 130. In an embodiment, the detector-to-object distance is varied to maintain the object at a virtual isocenter of the system 100. In an embodiment, the C-arm 110 and/or the source 120 and/or detector 130 on the C-arm 110 may be moved in any plane or not moved to position the object at the virtual isocenter in the field of view of the detector 130. Measurement of the varying detector-to-object and/or source-to-object distance allows the image processor 160 to compensate for the change in distance and thus the change in magnification. The tracker module 170 may use data from the EM sensor 140 and EM transmitter 150 or other tracking device to track the detector-to-object distance.

Alternatively, EM sensor 140 or EM transmitter 150 may be mounted on the source 120 with the EM transmitter 150 or EM sensor 140 on the object to determine position of the source 120. A position of the X-ray source 120 may be recorded and used with the source-to-detector distance to determine and account for the magnification change. Tracker module 170 may monitor a position of an instrument or tool used during a diagnostic or surgical procedure, for example.

The tracker module 170 monitors a position of object 112, X-ray detector 130, and/or X-ray source 120 in the system 100. The tracker module 170 may provide position data in a reference coordinate system with respect to object 112, source 120, and/or detector 130. The image processor 160 uses the position data when processing the image data to reconstruct 2D and/or 3D images. The position data may also be used for other purposes, such as surgical navigation, for example. In one embodiment, the tracker module 170 continuously calculates the positions of the X-ray detector 130 and object 112 with respect to a coordinate system defined relative to a coordinate system reference point or central axis. In at least one embodiment, the image processor 160 generates control or trigger commands to the X-ray source 120 or source controller to scan the object based on position data.

In at least one embodiment, the image processor 160 collects a series of image exposures from the detector 130 as the C-arm 110 is moved. The detector 130 receives an image exposure each time the X-ray source 120 is triggered. The image processor 160 combines image exposures with reference data, reconstructing a 3D volumetric data set for example. The 3D volumetric data set may be used to generate images, such as slices, or a region of interest from the object. For example, the image processor 160 may produce from the volumetric data sets sagittal, coronal, and/or axial views of a patient spine, knee, or other area. The image processor 160 may be implemented in software and/or hardware. It is contemplated that the image processor 160 may comprise a general purpose computer, a microprocessor, a microcontroller, and/or an application-specific integrated circuit, for example.

In one or more embodiments, 3D image reconstruction may be formed by combining successive slices or planes scanned of object 112 using a fan beam for example. A 3D image reconstruction may also be formed by rotating source 120 and detector 130 around object 112 to obtain cone or area beam projections of the object. In a cone beam projection, the object may be illuminated with a point source and X-ray flux measured on a plane by the detector 130. The distance from object 112 to the detector 130 and the distance from object 112 to the source 120 may be used to determine parallel projections for image reconstruction.

Filtered backprojection may also be used to reconstruct a 3D image based on filtering and backprojecting a plane in a cone beam. In a filtered backprojection, individual fan beam or cone beam projections are analyzed and combined to form a 3D reconstruction image. Fan beams are tilted out of a source-detector plane of rotation for analysis in a new coordinate system for filtered backprojection. Projection data is weighted based on distance and convolved. Then, the convolved weighted projections are backprojected over a 3D reconstruction grid to reconstruct a 3D image.

After the image(s) have been reconstructed, the image processor 160 may transmit the image(s) to the output 190. It is contemplated that output 190 may comprise a display, a printer, facsimile, electronic mail, a storage unit, or other medium, for example. The image(s) may be displayed and/or stored via the output 190 for use by a user such as a technician, physician, surgeon, other healthcare practitioner, or security officer. It is further contemplated that, in at least one embodiment, output 190 may comprise a laptop, a PDA, cell phone or other wireless device communicating wirelessly with image processing computer 160.

In operation, for example, a patient's mid-spinal area may be scanned in the system 100. The C-arm 110 may not reach all positions of a mid-spinal scan when the patient is positioned on a table, such as the positioner 180. Therefore, the C-arm 110 may be moved and positioned from a side. As the C-arm 110 is moved in a non-circular motion, the spine may not remain centered in scanned images because the path of the C-arm 110 may not be circular. The C-arm 110 may be moved, such as by raising and lowering the C-arm 110 on a C-arm support, to keep the spine in the center (e.g., a virtual isocenter).

As the C-arm 110 is moved and the spine is not moved, the spine is located closer or farther from X-ray source 120. Thus, obtained images have a different magnification from start to finish (for example, five vertebral levels in a first image to three vertebral levels in a last image due to more magnification) because the C-arm 110 moves in a non-circular arc. A change in magnification may be determined because position of the detector 130 with respect to the object being scanned is measured by the tracker module 170 using the EM transmitter 150 and sensor 140, for example. Then, the magnification change is taken into account during reconstruction of a 3D volume image of the mid-spinal area. Rather than using a fixed distance in standard image reconstruction algorithms, the variable distance values are used in reconstruction calculations for the image(s).

Figure 2:
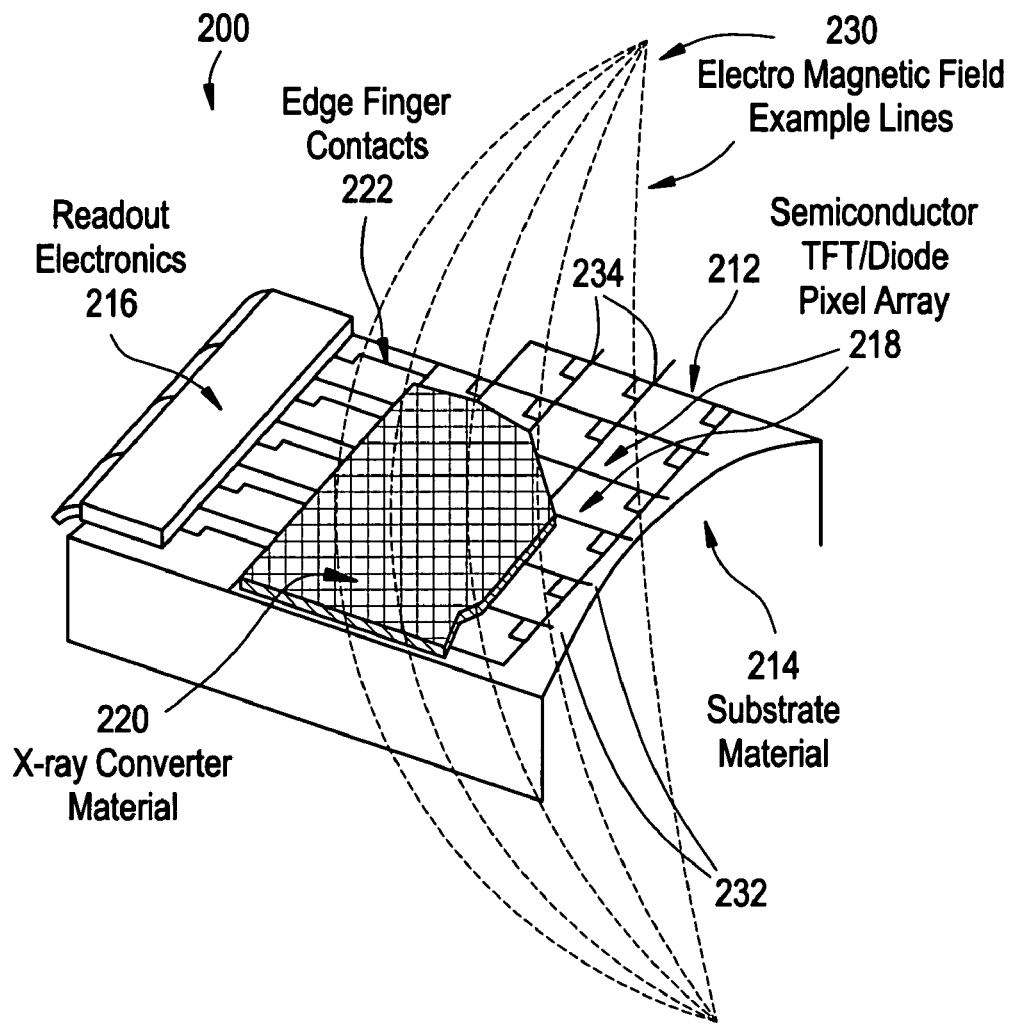
FIG. 2 illustrates a partially broken away perspective view of a known X-ray detector (a flat panel X-ray detector for example) adapted to be used with a medical imaigning system (similar to that illustrated in FIG. 1) in accordance with certain embodiments.

FIG. 2 illustrates a partially broken away view of a known implementation of an X-ray detector (a flat panel X-ray detector for example) generally designated 200, that may be used in a medical imaging system similar to that illustrated in FIG. 1 (X-ray detector 130 for example). In the illustrated embodiment, the flat panel detector 200 comprises a flat panel 212, a substrate material 214 and readout electronics 216 (off board readout electronics for example), which is electrically connected to a flat panel detector control (not shown). In the illustrated embodiment, flat panel 212 comprises a pixel array 218 (a semiconductor TFT/Diode pixel array for example) formed on an X-ray converter material 220 and one or more edge finger contacts 222 adapted to electrically couple at least the flat panel 212 to the readout electronics 216.

It is contemplated that the X-ray detector 200 may be affected by interfering fields (electric and/or magnetic fields for example). FIG. 2 illustrates a plurality of electromagnetic field lines 230 of a given frequency passing through the X-ray detector 200. It is contemplated that the electromagnetic field lines 230 may cause signal noise on at least the data lines 232. In particular, the electromagnetic field lines of force 230 may pass through at least one of the circuit loop of the TFT-diode, data line, analog-digital converter and ground return of the X-ray detector 200. This in turn may induce current to flow through at least the circuit loop, which is digitized by the detector as uncorrelated structured noise.

Figure 3:
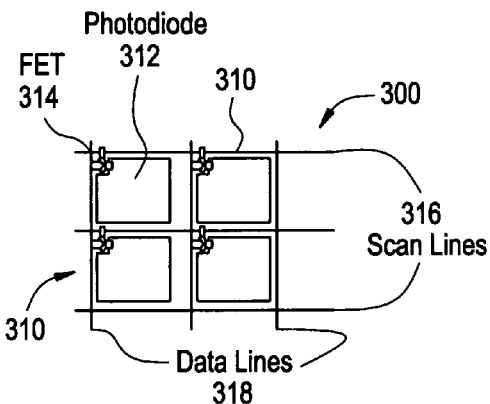
FIG. 3 illustrates a plan view of a cluster of four detector pixels (used with a flat panel X-ray detector for example) in accordance with certain embodiments.

FIG. 3 illustrates a plan view of a cluster, generally designated 300, of a plurality of detector pixels 310, forming a grid. FIG. 3 depicts four pixels 310, although a different number of pixels 310 are contemplated. In the illustrated embodiment, each detector pixel 310 comprises a photodiode 312 having a transistor switch 314 (a TFT-FET for example), where the transistor switch 314 enables effective multiplexing of the pixel array.

In one embodiment, cluster 300 further comprises a plurality of scan lines 316 and data lines 318. In at least one embodiment, at least one scan line 316 contacts to at least one data line 318. It is also contemplated that each scan line 316 may contact a plurality of data line 318 and/or each data line 318 may contact a plurality of scan lines 316. Further, at least one of the data lines 318 and the scan lines 316 are coupled to and communicate with at least one detector pixel 310. In at least one embodiment, each detector pixel 310 (comprising one photodiode 312 and TFT-FET 314) is coupled to and communicates with at least one of the data lines 318 and scan lines 316.

Figure 4:
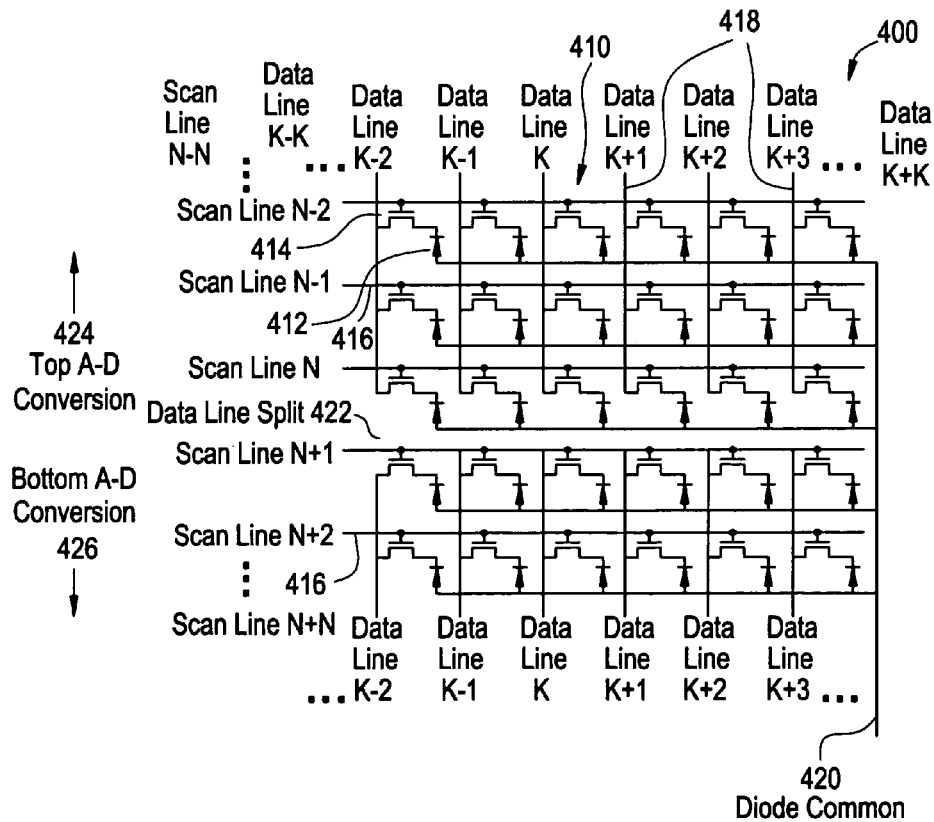
FIG. 4 illustrates a schematic representation of a TFT Photodiode array (used with a flat panel X-ray detector for example) in accordance with certain embodiments.

FIG. 4 illustrates a schematic representation of a TFT-Photodiode array generally designated 400 (used in a flat X-ray detector for example). In the illustrated embodiment array 400 comprises a plurality of detector pixels 410 data lines 418 and scan lines 416. In this embodiment, each detector pixel 410, comprises a transistor switch 414 (a TFT-FET for example) coupled to and communicating with at least one scan line 416 and one data line 418. Furthermore, the switch 414 is coupled to and communicates with a photodiode 412 which in turn is coupled to and communicates with a diode common 420. In one embodiment, a plurality of the photodiodes 412 are coupled to and communicate with diode common 420.

As illustrated, the analog data lines 418 are split such that each half line may be attached to off board analog-digital converters (not shown). Data line split 422 divides the array 400 into first or top and second or bottom A-D conversion 424 and 426 respectively.

As illustrated in FIG. 4, at least one of the top and bottom A-D conversions 424 and 426 comprise at least one of a plurality of scan lines and data lines 416 and 418. In the depicted embodiment, the first or top A-D conversion 424 comprises a plurality of scan lines 416 above the data line split 422 contacting one or more of the data lines 418. In one embodiment, top A-D conversion 424 comprises scan line N through scan line N–N which contacts and forms a grid patter with data lines K–K through data line K+K as illustrated.

Similarly, the second or bottom A-D conversion 426 comprises the plurality of scan lines 416 below the data line split 422 contacting one or more data lines 418. In one embodiment, bottom A-D conversion 426 comprise scan lines N+1 through scan line N+N contacting and forming a grid pattern with data lines K–K through data lines K+K as illustrated.

Figure 5:
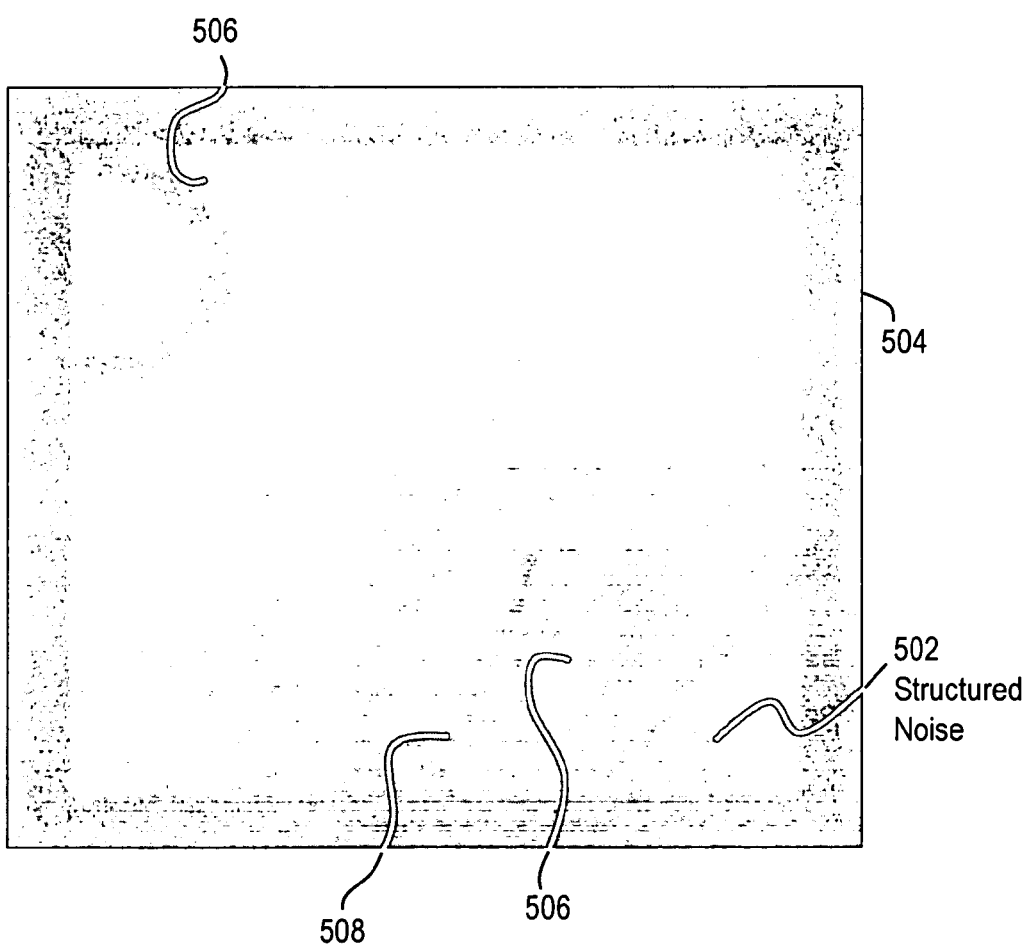
FIG. 5 illustrates an example of an image artifact that may be generated by an induced field passing through known X-ray detectors (similar to that illustrated in FIG. 2) in accordance with certain embodiments.

FIG. 5 illustrates an example of an image artifact, generally designated 500, that may be generated by an interfering field. It is contemplated that the generated image artifact 500 is dependent, at least in part, upon the induced field strength and frequency of the interfering field, overall detector size and orientation within the field. As illustrated in FIG. 5, the typical interference pattern may comprise one or more horizontal bars 502 rolling through the lower portion of the phantom X-ray image 504 which additionally may include at least one of circular and catheter anatomy patterns 506 and 508 respectively.

Figure 6:
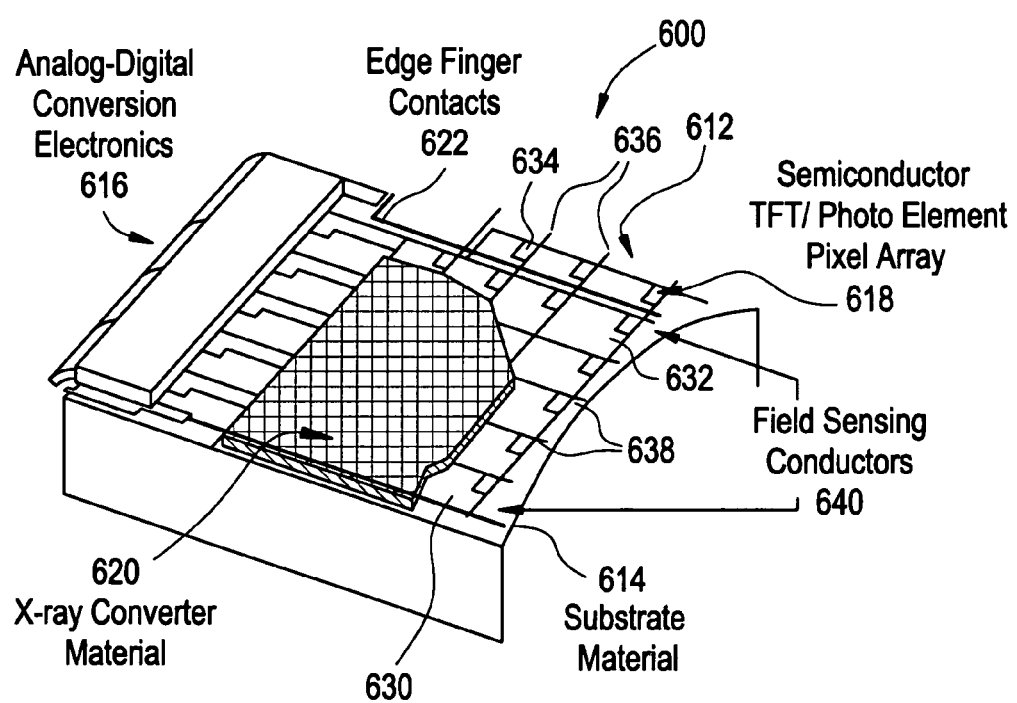
FIG. 6 illustrates a partially broken away perspective view of an X-ray detector (a flat panel X-ray detector for example) adapted to be used with a medical imaigning system (similar to that illustrated in FIG. 1) that is immune to or reduces the effect of interfering EM fields in accordance with certain embodiments.

FIG. 6 illustrates a partially broken away perspective view of an X-ray detector generally designated 600 (a flat panel X-ray detector for example) that is immune to or reduces the effects of interfering electrical and/or magnetic fields in accordance with certain embodiments. In particular, FIG. 6 illustrates a partially broken away view of a flat panel X-ray detector that may be used with an imaging system 100 similar to that illustrated in FIG. 1. It is contemplated that the X-ray detector 600 may be affected by electric and/or magnetic fields, where a plurality of electromagnetic field lines of a given frequency pass through X-ray detector 600, causing signal noise on at least the data lines. This in turn may induce current to flow through this circuit which may be digitized as uncorrelated structured noise.

In the illustrated embodiment, the flat panel detector 600 comprises a panel portion 612 having at least one field sensing conductor 640 adapted to locally reduce electrical and/or magnetic noise in the X-ray detector 600. X-ray detector 600 comprises at least panel portion 612 having a plurality of field sensing conductors 640, conversion portion 616 (which in at least one embodiment comprises an analog-digital conversion system similar to that provided below) and one or more edge finger contacts 622 connecting the conversion and panel portions 616 and 612 respectively. In one embodiment, panel portion 612 further comprises substrate material 614, X-ray material 620 and pixel array 618 formed on X-ray material 620. At least one embodiment of pixel array 618 comprises at least one semi-conductor TFT/Photo element 630 (a plurality of semi-conductor TFT/Photo elements 630 are illustrated).

In the embodiment illustrated in FIG. 6, each semi-conductor TFT/Photo element 630 comprises a photodiode 632 having a transistor switch 634 (a TFT-FET for example), where the transistor switch 634 enables effective multiplexing of the pixel array 618.

As illustrated, panel portion 612 further comprises a plurality of scan lines 636 and data lines 638. In at least one embodiment, at least one scan line 636 contacts at least one data line 638. It is also contemplated that each scan line 636 may contact a plurality of data line 638 and/or each data line 638 may contact a plurality of scan lines 636, forming a grid. Further, at least one of the data lines 638 and the scan lines 636 are coupled to and communicate with at least one detector pixel 630. In at least one embodiment, each detector pixel 630 (comprising one photodiode 632 and TFT-FET 634) is coupled to and communicates with at least one of the data lines 638 and scan lines 636.

One embodiment comprises X-ray detector 600 having one or more field sensing conductors 640 in the same orientation as at least one of the data lines 638. The number and spacing of the field sensing conductors is determined, based at least in part, by the interfering filed as provided below. It is contemplated that in at least one embodiment, field sensing conductors 640 may be oriented in the direction of the scan lines 636, as well as the direction of the data lines 638. The interfering field is sampled locally by one or more of these conductors 640, which in at least one embodiment has essentially the same resistance and capacitance as at least one of the data lines 638.

Figure 7:
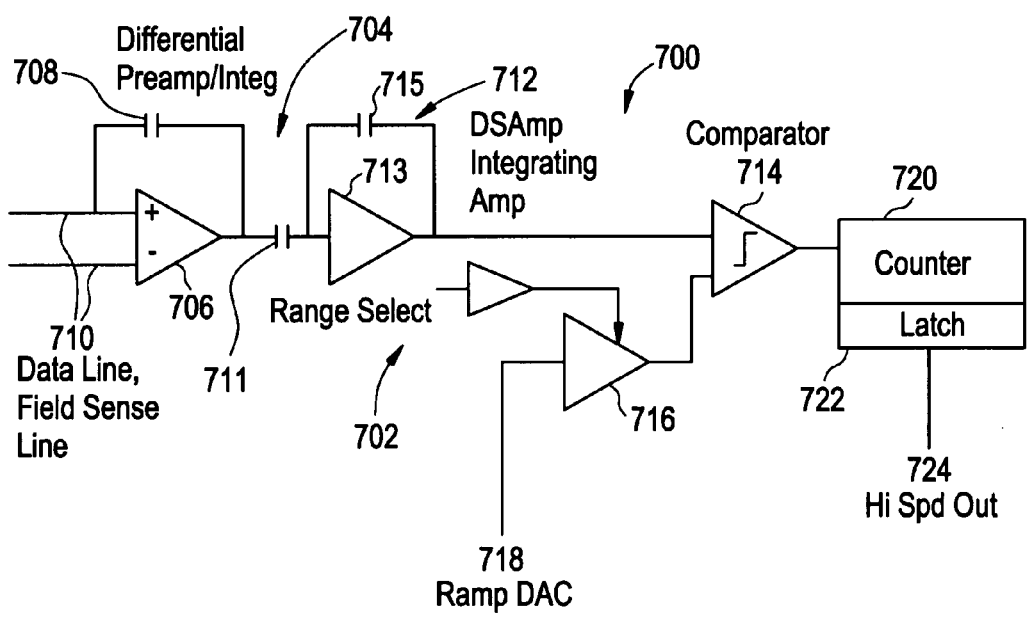
FIG. 7 illustrates a schematic representation of an analog-digital conversion system or module used with an X-ray detector (similar to that illustrated in FIG. 6) in accordance with certain embodiments.

FIG. 7 illustrates a schematic representation of an analog-digital conversion system or module generally designated 700, used with an X-ray detector (similar to that illustrated in FIG. 6) in accordance with certain embodiments. In this embodiment, the analog-digital conversion system 700 comprises an analog to digital module 702 and a differential preamplification module 704 adapted to subtract noise detected by at least one of the field sensing conductors (similar to the field sensing conductors as provided above with respect to FIG. 6). Although the depicted module comprises an integrating style A-D conversion, any converter architecture is contemplated. For example, the interfering field may be sensed and digitized separately and then subtracted from a pixel value samples using digital processing.

In the illustrated embodiment, the amplitude/magnitude of the interfering field is sensed and subtracted in the first analog stage prior to conversion. The amplitude/magnitude of the interfering field is subtracted out using differential preamp/integ module 704 (where differential preamp/integ module 704 comprises op amp 706 and capacitor 708). In at least one embodiment, the differential preamp/integ module 704 has data and field sense lines 710 as inputs. The output of the differential preamp/integ module 704 is coupled to DSAmp integrating amp 712 through capacitor 711 (where the DSAmp integrating amp 712 comprises op amp 713 and capacitor 715).

In this embodiment, the A-D conversion module 702 further comprises the output of the DSAmp integrating amp 712 coupled to and communicating with comparator 714. A range selectable amp 716, having a ramp DAC 718 as input, has an output coupled to comparator 714. Comparator 714 is further coupled to a counter 720 and latch 722 having high speed out 724.

Figure 8:
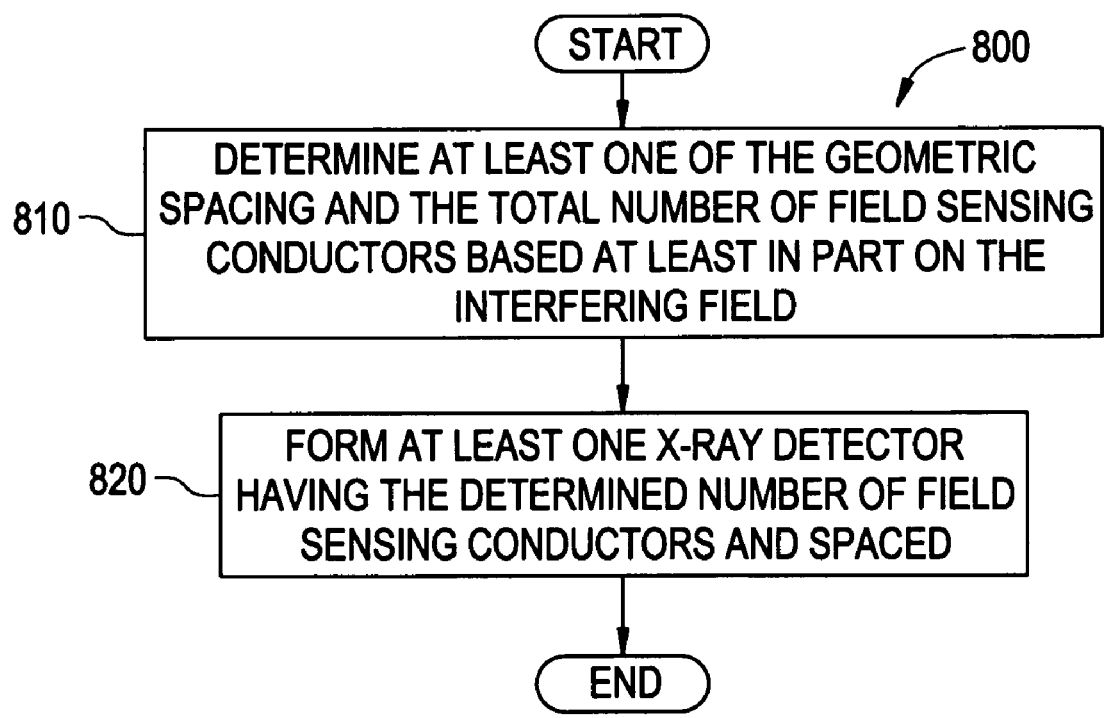
FIG. 8 illustrates a high level flow diagram depicting a method of forming an X-ray detector (similar to that illustrated in FIG. 6) adapted to be used with a medical imagining system (similar to that illustrated in FIG. 1) in accordance with certain embodiments.

Referring to FIG. 8, a high level flow diagram depicting a method of programming an X-ray detector, generally designated 800 (a flat panel X-ray detector for example) that eliminates or reduces the effects of an interfering EM field is illustrated. In at least one embodiment, an electronic and/or magnetic field magnitude may be sampled locally (within the same orientation as the flat panel of the X-ray detector for example) and subtracted out of each respective element sample. In the depicted embodiment, method 800 comprises block 810, determining at least one of the geometric spacing and total number of field sensing conductors based at least in part on the interfering electrical and/or magnetic field. Method 800 further comprises block 820, forming at least one X-ray detector (a flat panel X-ray detector for example) having the determined number of field sensing conductors and spacing.

Figure 9:
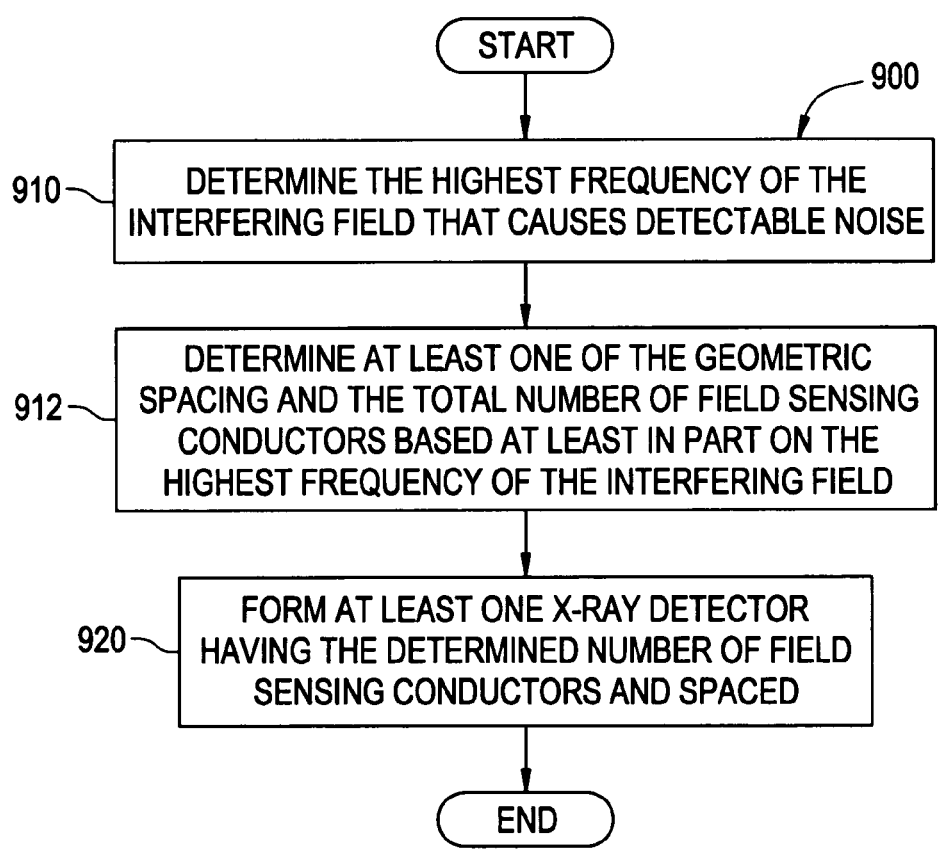
FIG. 9 illustrates a detailed flow diagram depicting a method of forming an X-ray detector (similar to that illustrated in FIG. 6) adapted to be used with a medical imagining system (similar to that illustrated in FIG. 1) in accordance with certain embodiments.

FIG. 9 illustrates a detailed flow diagram depicting a method, generally designated 900, of forming an X-ray detector (a flat panel X-ray detector for example) that reduces or eliminates the effects of interfering EM field. Method 900 comprises 910, determining a highest frequency of the interfering field that causes detectible noise. In at least one embodiment, the method may comprise determining the interfering field that causes detectable noise, then determining the highest frequency of such field. Block 912 comprises at least one of the geometric spacing in the total number of field sensing conductors is determined based at least in part on the highest frequency of the interfering field. In one embodiment, both the total number of field sensing conductors and spacing thereof is determined. Method 900 further comprises 920 forming at least one X-ray detector having such determined number of field sensing conductors and spacing.

Figure 10:
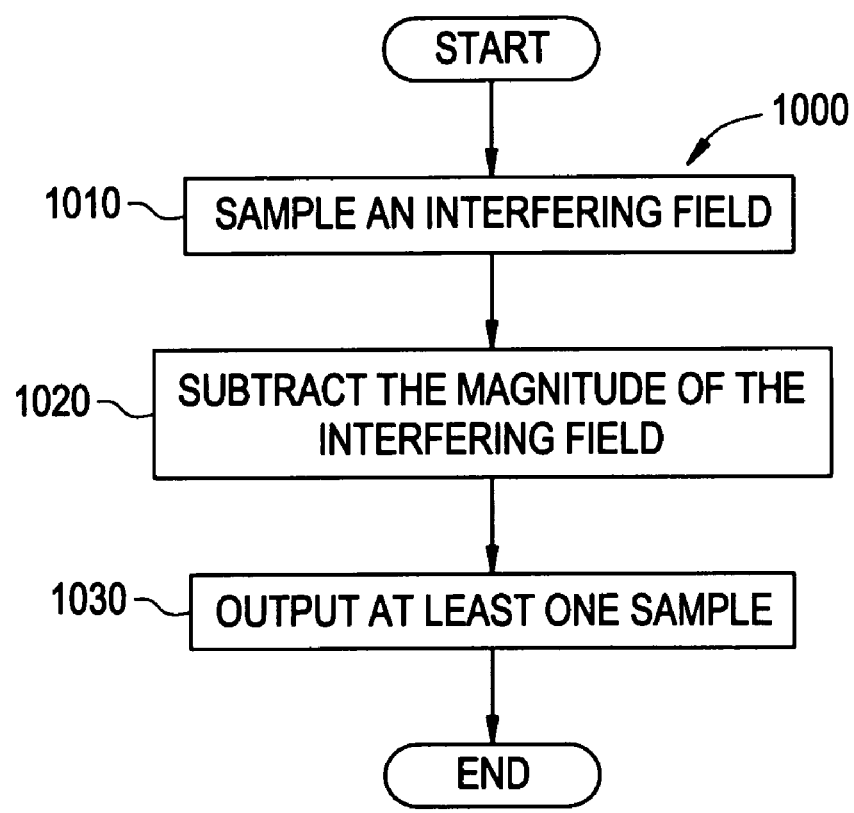
FIG. 10 illustrates a high level flow diagram depicting a method of using an X-ray detector (similar to that illustrated in FIG. 6) adapted to be used with a medical imagining system (similar to that illustrated in FIG. 1) in accordance with certain embodiments.

Referring to FIG. 10, a high level flow diagram depicting a method, generally designated 1000, of using an X-ray detector (a flat panel X-ray detector for example) used in an imaging system (similar to that provided previously) is illustrated. In at least one embodiment, the X-ray detector reduces or eliminates the effects of interfering electrical and/or magnetic field. Method 1000 comprises block 1010, sampling at least one interfering field. In at least one embodiment, the interfering electrical and/or magnetic field is sampled locally (within the same orientation as the flat panel of the X-ray detector for example). Embodiments of method 1000 further comprise block 1020, subtracting the magnitude of the interfering field. The field amplitude/magnitude of the interfering field is subtracted out in a preamplification stage in the X-ray detector conversion electronics. It is also contemplated that the amplitude/magnitude of the interfering field may be digitized and then subtracted out using digital processing. Method 1000 further comprises block 1030, outputting at least one sample.

FIG. 11 illustrates a detailed flow diagram depicting a method, generally designated 1100, of using an X-ray detector (a flat panel X-ray detector for example) used in an imaging system (similar to that provided previously) is illustrated. In at least one embodiment, the X-ray detector reduces or eliminates the effects of the interfering electrical and/or magnetic field. Method 1100 comprises block 1110 locally sampling an interfering field using at least one field sensing conductor. In at least one embodiment, the interfering electrical and/or magnetic field is sampled locally (within the same orientation as the flat panel of the X-ray detector for example). Embodiments comprise block 1112, determining a magnitude of the interfering field and 1120 subtracting the magnitude of the sample field from each respective sample respectively. The field amplitude/magnitude of the interfering field is subtracted out in a preamplification stage in the X-ray detector conversion electronics. It is also contemplated that the amplitude/magnitude of the interfering field may be digitized and then subtracted out using digital processing. This method 1100 may further comprise block 1130, outputting at least one sample having a reduced or eliminated electric and/or magnetic field.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for reducing electromagnetic noise induced in an X-ray detector comprising:
   sampling an interfering electromagnetic field in the X-ray detector using at least one field sensing conductor formed in the X-ray detector;
   measuring X-ray radiation at the X-ray detector;
   subtracting a magnitude of said interfering field from at least one output of the X-ray detector; and
   outputting at least one X-ray detector output having reduced electromagnetic noise.

2. The method of claim 1 wherein said interfering field is sampled within a same orientation as the X-ray detector.

3. The method of claim 1 comprising subtracting said magnitude of said interfering field from a plurality of X-ray detector pixels within the X-ray detector.

4. The method of claim 1 comprising subtracting said magnitude of said interfering field using an analog-digital conversion system.

5. The method of claim 4 wherein subtracting said magnitude of said interfering field comprises subtracting said magnitude in a pre-amplification stage of said analog-digital conversion system.

6. The method of claim 1 wherein subtracting said magnitude of said interfering field comprises digitizing said magnitude of said interfering field and then subtracting said magnitude using digital processing.

7. The method of claim 1 wherein the X-ray detector is used in a medical imaging system.

8. A method of forming an X-ray detector used in a medical imaging system comprising:
   determining at least one of a number of electromagnetic field sensing conductors and a spacing of said electromagnetic field sensing conductors based at least in part on an interfering electromagnetic field; and forming the X-ray detector having said determined number of field sensing conductors and said determined spacing.

9. The method of claim 8 comprising determining a highest frequency of said interfering field.

10. The method of claim 8 comprising adding said field sensing conductors in a same orientation as at least one of data and scan lines formed in said X-ray detector.

11. A method of forming an X-ray detector used in a medical imaging system comprising:
   determining at least one of a number of electromagnetic field sensing conductors and a spacing of said electromagnetic field sensing conductors based at least in part on an interfering electromagnetic field;
   determining a highest frequency of said interfering field;
   spacing said sensing conductors a minimum of one fourth of a wavelength of said highest frequency of said interfering field; and
   forming the X-ray detector having said determined number of field sensing conductors and said determined spacing.

12. An X-ray detector used in a medical imaging system, the X-ray detector comprising:
   a panel portion having at least one X-ray detector pixel and at least one electromagnetic field sensing conductor, wherein said field sensing conductor measures an interfering electromagnetic field in the X-ray detector; and
   a electromagnetic noise reduction component capable of adjusting the output of at least one said X-ray detector pixel based on said interfering electromagnetic field.

13. The X-ray detector of claim 12 further comprising a plurality of electromagnetic field sensing conductors.

14. The X-ray detector of claim 12 wherein said interfering field may be sampled within a same orientation as the panel portion.

15. The X-ray detector of claim 12 wherein said field sensing conductor is formed on said panel portion in a same orientation as at least one of a data line and scan line in said panel portion.

16. The X-ray detector of claim 12 wherein said electromagnetic noise reduction component comprises an analog-digital conversion system adapted to subtract out a magnitude of said interfering field.

17. The X-ray detector of claim 16 wherein said magnitude of said interfering field is subtracted out in a pre-amplification stage in said analog-digital conversion system.

18. The X-ray detector of claim 12 wherein said analog-digital conversion system comprises a digital processing system adapted to digitize said magnitude of said interfering field and then subtracting out said magnitude using digital processing.

19. An X-ray detector used in a medical imaging system, the X-ray detector comprising:
   a panel portion having at least one X-ray detector pixel and a plurality of electromagnetic field sensing conductors, wherein said field sensing conductors measure an interfering electromagnetic field in the X-ray detector; and
   a electromagnetic noise reduction component capable of adjusting the output of at least one said X-ray detector pixel based on said interfering electromagnetic field,
   wherein at least one of said field sensing conductors is spaced a minimum of one fourth of a wavelength of a highest frequency of said sample interfering field from another of said field sensing conductors.

* * * * *